(12) United States Patent
Widomski et al.

(10) Patent No.: US 7,842,069 B2
(45) Date of Patent: Nov. 30, 2010

(54) INFLATABLE OCCLUDER

(75) Inventors: David R. Widomski, Wakefield, MA (US); Steven W. Opolski, Carlisle, MA (US); Andrzej J. Chanduszko, Chandler, AZ (US); Carol A. Devellian, Topsfield, MA (US)

(73) Assignee: NMT Medical, Inc., Boston, MA (US)

( * ) Notice: Subject to any disclaimer, the term of this patent is extended or adjusted under 35 U.S.C. 154(b) by 647 days.

(21) Appl. No.: 11/123,871

(22) Filed: May 6, 2005

(65) Prior Publication Data

US 2005/0288706 A1  Dec. 29, 2005

Related U.S. Application Data

(60) Provisional application No. 60/569,213, filed on May 7, 2004.

(51) Int. Cl.
*A61B 17/08* (2006.01)
(52) U.S. Cl. ....................................................... 606/213
(58) Field of Classification Search ................. 606/213, 606/194, 195, 215, 216–218, 151; 623/23.72; 604/103.08–103.09; 600/207
See application file for complete search history.

(56) References Cited

U.S. PATENT DOCUMENTS

| | | | | |
|---|---|---|---|---|
| 3,874,388 A | * | 4/1975 | King et al. | 606/232 |
| 4,007,743 A | | 2/1977 | Blake | |
| 4,836,204 A | * | 6/1989 | Landymore et al. | 606/215 |
| 4,917,089 A | * | 4/1990 | Sideris | 606/215 |
| 5,108,420 A | | 4/1992 | Marks | |
| 5,192,301 A | | 3/1993 | Kamiya et al. | |
| 5,284,488 A | | 2/1994 | Sideris | |
| 5,334,217 A | * | 8/1994 | Das | 606/213 |
| 5,366,478 A | * | 11/1994 | Brinkerhoff et al. | 606/213 |
| 5,413,571 A | * | 5/1995 | Katsaros et al. | 606/213 |
| 5,425,744 A | | 6/1995 | Fagan et al. | |
| 5,433,727 A | | 7/1995 | Sideris | |
| 5,451,235 A | | 9/1995 | Lock et al. | |
| 5,507,811 A | | 4/1996 | Koike et al. | |
| 5,620,461 A | | 4/1997 | Van De Moer et al. | |
| 5,634,936 A | | 6/1997 | Linden et al. | |
| 5,645,566 A | * | 7/1997 | Brenneman et al. | 606/213 |
| 5,656,013 A | * | 8/1997 | Yoon | 600/207 |
| 5,683,411 A | | 11/1997 | Kavteladze et al. | |
| 5,702,421 A | | 12/1997 | Schneidt | |
| 5,709,707 A | | 1/1998 | Lock et al. | |
| 5,725,552 A | | 3/1998 | Kotula et al. | |
| 5,733,294 A | | 3/1998 | Forber et al. | |
| 5,741,297 A | | 4/1998 | Simon | |
| 5,797,960 A | * | 8/1998 | Stevens et al. | 606/213 |
| 5,861,003 A | * | 1/1999 | Latson et al. | 606/213 |

(Continued)

FOREIGN PATENT DOCUMENTS

WO   WO 98/07375   2/1998

(Continued)

*Primary Examiner*—Gary Jackson
*Assistant Examiner*—Son Dang
(74) *Attorney, Agent, or Firm*—Helen S. Liu

(57) ABSTRACT

An implant for occluding a septal defect, such as a patent foramen ovale (PFO), and methods of delivering the implant are described. The implant includes a scaffold, at least one channel, and an injection port in fluid communication with the channels for inflating the scaffold.

19 Claims, 12 Drawing Sheets

U.S. PATENT DOCUMENTS

| | | | |
|---|---|---|---|
| 5,879,366 A | | 3/1999 | Shaw et al. |
| 5,904,703 A | * | 5/1999 | Gilson ........................ 606/213 |
| 5,919,200 A | | 7/1999 | Stambaugh et al. |
| 5,928,250 A | | 7/1999 | Koike et al. |
| 5,944,738 A | | 8/1999 | Amplatz et al. |
| 5,964,781 A | * | 10/1999 | Mollenauer et al. ......... 606/213 |
| 5,976,174 A | * | 11/1999 | Ruiz ........................... 606/213 |
| 6,024,756 A | | 2/2000 | Huebsch et al. |
| 6,056,760 A | | 5/2000 | Koike et al. |
| 6,080,182 A | | 6/2000 | Shaw et al. |
| 6,113,609 A | * | 9/2000 | Adams ........................ 606/139 |
| 6,117,159 A | | 9/2000 | Huebsch et al. |
| 6,171,329 B1 | | 1/2001 | Shaw et al. |
| 6,174,322 B1 | | 1/2001 | Schneidt |
| 6,206,907 B1 | | 3/2001 | Marino et al. |
| 6,214,029 B1 | | 4/2001 | Thill et al. |
| 6,221,092 B1 | | 4/2001 | Koike et al. |
| 6,270,515 B1 | * | 8/2001 | Linden et al. ................ 606/213 |
| 6,290,674 B1 | | 9/2001 | Roue et al. |
| 6,312,446 B1 | | 11/2001 | Huebsch et al. |
| 6,324,064 B1 | | 11/2001 | Schneider |
| 6,355,052 B1 | | 3/2002 | Neuss et al. |
| 6,371,974 B1 | * | 4/2002 | Brenneman et al. ......... 606/213 |
| 6,375,671 B1 | | 4/2002 | Kobayashi et al. |
| 6,379,368 B1 | | 4/2002 | Corcoran et al. |
| 6,402,772 B1 | | 6/2002 | Amplatz et al. |
| 6,440,152 B1 | * | 8/2002 | Gainor et al. ................ 606/213 |
| 6,482,224 B1 | | 11/2002 | Michler et al. |
| 6,596,013 B2 | | 7/2003 | Yang et al. |
| 6,623,508 B2 | | 9/2003 | Shaw et al. |
| 6,939,348 B2 | * | 9/2005 | Malecki et al. ................ 606/41 |
| 7,025,776 B1 | * | 4/2006 | Houser et al. ............... 606/213 |
| 7,338,514 B2 | * | 3/2008 | Wahr et al. .................. 606/213 |
| 7,632,291 B2 | * | 12/2009 | Stephens et al. ............. 606/195 |
| 7,695,488 B2 | * | 4/2010 | Berenstein et al. .......... 606/194 |
| 2002/0010481 A1 | | 1/2002 | Jayaraman et al. |
| 2002/0077555 A1 | | 6/2002 | Schwartz |
| 2002/0107531 A1 | | 8/2002 | Schreck et al. |
| 2002/0147462 A1 | * | 10/2002 | Mair et al. ................... 606/213 |
| 2002/0183786 A1 | | 12/2002 | Girton |
| 2002/0183787 A1 | * | 12/2002 | Wahr et al. ................... 606/213 |
| 2003/0028213 A1 | | 2/2003 | Thill et al. |
| 2003/0045893 A1 | | 3/2003 | Ginn |
| 2003/0055455 A1 | * | 3/2003 | Yang et al. ................... 606/215 |
| 2003/0100920 A1 | | 5/2003 | Akin et al. |
| 2003/0139819 A1 | | 7/2003 | Beer et al. ................. 623/23.71 |
| 2003/0208232 A1 | * | 11/2003 | Blaeser et al. ............... 606/213 |
| 2004/0092973 A1 | * | 5/2004 | Chanduszko et al. ......... 606/151 |
| 2004/0254594 A1 | * | 12/2004 | Alfaro ......................... 606/151 |
| 2005/0288706 A1 | * | 12/2005 | Widomski et al. ........... 606/213 |
| 2006/0167494 A1 | * | 7/2006 | Suddaby ...................... 606/213 |
| 2007/0135831 A1 | * | 6/2007 | Burnett ....................... 606/192 |

FOREIGN PATENT DOCUMENTS

| | | |
|---|---|---|
| WO | WO 99/18862 | 4/1999 |
| WO | WO 99/18864 | 4/1999 |
| WO | WO 99/18870 | 4/1999 |
| WO | WO 99/18871 | 4/1999 |
| WO | WO 03/022159 | 3/2003 |

* cited by examiner

US 7,842,069 B2

INFLATABLE OCCLUDER

CROSS REFERENCE TO RELATED APPLICATIONS

This application claims benefit and priority to U.S. Provisional Application 60/569,213 filed May 7, 2004 the entirety of which is incorporated by reference herein.

FIELD OF THE INVENTION

The invention generally relates to inflatable occluders for correcting a septal defect, such as a patent foramen ovale (PFO).

BACKGROUND OF THE INVENTION

A patent foramen ovale (PFO) is a persistent, one-way, usually flap-like opening in the wall between the right atrium and left atrium of the heart. Since left atrial (LA) pressure is normally higher than right atrial (RA) pressure, the flap typically stays closed. Under certain conditions, however, RA pressure can exceed LA pressure, creating the possibility for right to left shunting of blood that can allow blood clots to enter the systemic circulation. In utero, the foramen ovale serves as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: the septum primum and septum secundum. However, autopsy studies have shown that a probe-detected patent foramen ovale (PFO) persists in up to approximately 25% of adults. Using contrast echocardiography (TEE), a patent foramen ovale can also be detected in approximately 25% of adults.

Studies have confirmed a strong association between the presence of a PFO and the risk for paradoxical embolism or stroke. Although the cause of ischemic stroke is not known in approximately 40% of cases, paradoxical embolism via a PFO is considered in the diagnosis, especially in young patients. In addition, there is evidence that patients with PFO and paradoxical embolism are at increased risk for future, recurrent cerebrovascular events.

Although the presence of a PFO has no therapeutic consequence in an otherwise healthy adult, patients suffering a stroke or transient ischemic attack (TIA) in the presence of a PFO and without another cause of the ischemic stroke are considered for prophylactic therapy to reduce the risk of a recurrent embolic event. These patients are commonly treated with oral anticoagulants, which have potential adverse side effects, such as hemorrhaging, hematoma, and interactions with a variety of other drugs. In certain cases, such as when anticoagulation is contraindicated, surgery may be used to close a PFO. Suturing a PFO closed typically requires attachment of the septum secundum to the septum primum with either continuous or interrupted sutures under direct visualization or via port access surgery.

Nonsurgical closure of PFOs has become possible with the advent of umbrella devices and a variety of other similar mechanical closure designs, developed initially for percutaneous closure of atrial septal defects (ASD). These devices allow patients to avoid the potential side effects often associated with anticoagulation therapies. However, currently available designs of septal closure devices present drawbacks, such as technically complex implantation procedures, high complication rates (for example, thrombi, fractures, conduction system disturbances, perforations, and residual leaks), a high septal profile, large masses of foreign material, and lack of anatomic conformability, since most septal closure devices were originally designed to close ASDs, which are true holes, rather than the flap-like anatomy of a PFO. In addition, some septal closure devices are complex to manufacture, which can result in lack of consistency in product performance.

A need therefore exists for a septal closure device or occluder that can provide complete closure of a PFO in a minimum amount of time, that has a lower complication rate, and that is simple and inexpensive to use and manufacture.

SUMMARY OF THE INVENTION

The invention relates generally to a device and methods for occluding a septal defect, such as a patent foramen ovale (PFO).

In one aspect, the invention relates to an inflatable occluder capable of permanently closing for example, an intracardiac septal defect. In an embodiment, the inflatable occluder is a medical implant including a scaffold, the scaffold enclosing at least one inflatable channel, and an injection port in fluid communication with the channel. The scaffold may also have at least one structural member that provides a structure to the scaffold such that, when the channels are inflated, the scaffold adopts a shape that is capable of occluding a septal defect or other tissue defect that requires occlusion.

In an embodiment, the occluder includes at least one injection port and two scaffolds that are in fluid communication, or act independently from one another (e.g., are not in fluid communication), via at least one channel. Introduction of a fluid material into the injection port expands the channels which expands one or both scaffolds.

In one embodiment, the scaffold is made of a polymer material, for example, a bioresorbable material or a non-resorbable material. The polymer may be, for example, a non-bioresorbable polymer such as polyethylene, polyetheramide block copolymer (e.g., PEBAX®, Atofina Chemicals, Philadelphia, Pa.), polyurethane, fluorinated ethylene propylene, expanded polytetrafluorothylene (EPTFE), polyester fabric, polyvinyl alcohol, or a bioresorbable polymer, such as polylactic acid, polyethylene glycol, or polyglycolic acid, polycaprolactone, and polydioxanone. The scaffold may be formed of a solid film, semi-porous film or of a knitted or woven mesh, for example.

In an embodiment, the scaffold includes a first layer and a second layer. At least a portion of either the first or second layer may be made of the same or different materials. In an embodiment, at least a portion of the first layer may differ from the second layer in at least one mechanical property, for example, tensile strength, flex modulus, extension to break, thickness, durometer, surface geometry, and/or cross section. In certain embodiments, at least a portion of one of the layers is less flexible than at least a portion of one of the other layers.

In a particular embodiment, the first layer or second layer of the scaffold contains an adhesive, such as, for example, cyanocrylate, fibrin based adhesive, light activated adhesive, such as, for example, FocalSeal™ (Genzyme, Cambridge, Mass.), albumin, gluteraldehyde based adhesive, PEG polymer based adhesive, and marine derived adhesive for adhering the scaffold(s) to the patient's septal defect.

The scaffold may be any geometry, including square, polygonal, substantially circular, or non-circular. In a particular embodiment, the scaffold, when inflated, is sized and shaped to occlude a PFO. In one embodiment, the scaffold, when inflated, is sized and shaped to occlude a defect such as an ASD, a ventricular septal defect (VSD), a left atrial appendage (LAA), or a patent ductus arteriosus (PDA). In certain embodiments, the occluder may be used to occlude a defect in the wall of the bladder, bowel, stomach, esophagus, tracheobronchial tree or cerebral ventricular system, as well as to block or fill an artery, vein, ureter, lymphatic vessel, branch of the tracheobronchial tree, or any other vessel-like structure.

The scaffold channels may be any shape, such as, for example, linear, circular, cross-shaped, spiral-shaped, or star-shaped. The injection port in fluid communication with a channel, may for example, include a connection member, such as a threaded connection, a break-away connection, or a simple quick connection similar to the connections used in vacuum pumps, and compressed air fittings, for example, such that the occluder can be reversibly attached to an elongated member or catheter and recaptured for delivering the occluder into the heart of a patient. In an embodiment, the injection port includes, for example, a one-way valve to prevent back flow of fluid out of the channel. An exemplary one-way valve is a self healing membrane similar to those in needle injection ports of intravenous solution bags, or alternatively, a check valve.

In an embodiment, the occluder includes a structural member that provides support to the scaffold when the scaffold is inflated. For example, the structural member provides a shape to the scaffold that allows the scaffold to occlude a PFO when the channels of the occluder are inflated. The shape of the structural member may be curved to enhance a seal established between the scaffold and the heart tissue. In an embodiment, the structural member may be attached at a fixed end near the injection port at the center of the scaffold and distributed radially on the scaffold. In another embodiment, the structural member includes a portion of the scaffold that is thicker (e.g., reinforced or otherwise has a higher tensile strength) relative to other portions of the scaffold. In an alternative embodiment, the structural member or scaffold material is compliant and bends due to the force exerted by the inflated channels. The structural member may be made of a polymer, such as, for example, polyethylene, polyetheramide block copolymer (e.g., PEBAX®, Atofina Chemicals Philadelphia, Pa.), polyurethane, and fluorinate ethylene propylene. Alternatively, the structural member may be made of a metal or alloy, such as, for example, nitinol, stainless steel, MP35n, and magnesium or tungsten. The structural member may be temporary (e.g., bioresorbable) or may be permanent (e.g., non-bioresorbable).

In a particular embodiment, the invention provides an occluder in which the one or more channels of the scaffold accept material introduced into the channel. The scaffold may be at least partially inflated or expanded by the presence of the injected material in the one or more channels. In a particular embodiment, the injected material is a fluid, such as a flowable polymeric material, when injected into the channels, but solidifies in situ by, for example, a change in pH or ionic concentration of the polymer, exposure to organic solvents, introduction of a secondary material capable of precipitation, or exposure of the material in the one or more channels to heat or light, for example, a laser. The occluder may be hardened through a cooperative effect of coagulation, precipitation, or ionization of the patient's blood in the region of the occluder. The occluder may also feature bioresorbable materials impregnated with growth factors, mitogenic factors, or other determinants which can improve tissue growth such that tissue ingrowth can occur over a period of time. In yet another embodiment, the one or more channels contain pores that allow an adhesive to flow out of the one or more channels to the exterior surface of the scaffold adjacent to the tissue when the adhesive is injected into the channels of the occluder. The adhesive adheres the scaffold to the tissue.

In another embodiment, the channels comprise at least one flush port for flushing out air or fluid. In a particular embodiment, the flush port is located at the distal end of at least one channel and may include a valve, e.g., a one-way valve.

In another aspect, the invention provides methods for positioning an inflatable occluder in the heart of a patient's body. A sheath having a lumen and a catheter that is slideably receivable in the lumen of the sheath is attached to an occluder via a coupling mechanism positioned at the distal end of the catheter. The occluder is releasably joined to the catheter by the coupling mechanism allowing the occluder to detach from the catheter once it has been placed in the heart, e.g., the left atrium, the right atrium, or both. The occluder includes a scaffold that includes at least one channel and an injection port in fluid communication with at least one channel. The scaffold may also have at least one structural member for providing support to the scaffold once the occluder is inflated. The occluder is delivered to a site in the heart of the patient that requires occlusion, such as a septal defect, via a percutaneous transluminal route, for example, the femoral vein. Once positioned, the occluder is inflated by injecting a fluid into the injection port via the catheter and thereby into the one or more channels of the scaffold, whereby the scaffold adapts a shape that is suitable for occluding the septal defect. In certain embodiments, additional, i.e., second materials are injected into the channels via the catheter to aid in solidifying the first injected material. The catheter is detached from the occluder and the sheath and catheter are removed from the patient. In a particular embodiment, the occluder may remain permanently in the patient's heart. Alternatively, the occluder is bioresorbed by the patient's tissues.

In an embodiment, the occluder according to the invention, includes a scaffold that is delivered by the percutaneous transluminal route to the anatomical site of the defect, e.g., a PFO, and inflated in the left atrium to occlude the septal defect. In another embodiment, the occluder includes a scaffold that is delivered and inflated in the right atrium to occlude the septal defect. In a particular embodiment, the occluder includes two tissue scaffolds, one of which is delivered to the left atrium in the region of the septal defect and inflated and one of which is delivered to the right atrium in the region of the septal defect and inflated.

BRIEF DESCRIPTION OF THE DRAWINGS

In the drawings, like reference numbers generally refer to the same parts throughout the different views. Also, the drawings are not necessarily to scale, emphasis instead generally being placed upon illustrating the principles of the invention.

DETAILED DESCRIPTION OF THE INVENTION

The invention provides inflatable implants such as a septal occluder and their methods of use for permanently closing a septal defect, such as a patent foramen ovale (PFO). The septal occluder according to the invention has at least one scaffold, one or more channels, and an injection port. In a particular embodiment, the scaffold also has at least one structural member to provide an optimal shape for the scaffold for occluding a PFO. The term inflatable as used herein means capable of inflation or expansion with a fluid or a gas.

Figure 1A:
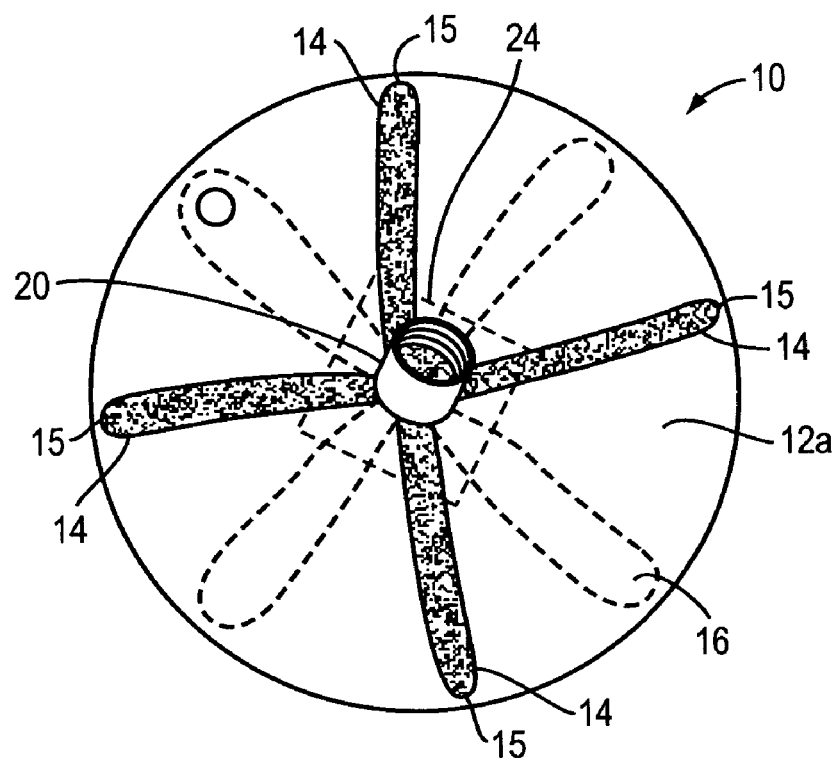
FIG. 1A is a front view of an illustrative embodiment of an inflatable occluder of the invention including a scaffold, four channels, four structural members, and an injection port.
Figure 2A:
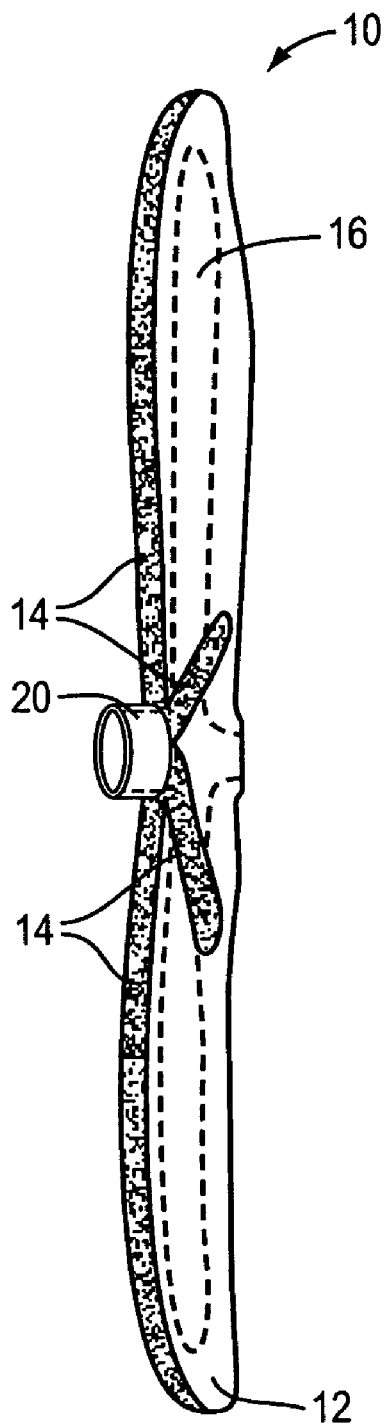
FIG. 2A is a side view of an embodiment of an inflatable occluder of the invention showing a single scaffold, which is not inflated, at least one channel, four structural members, and an injection port.
Figure 2B:
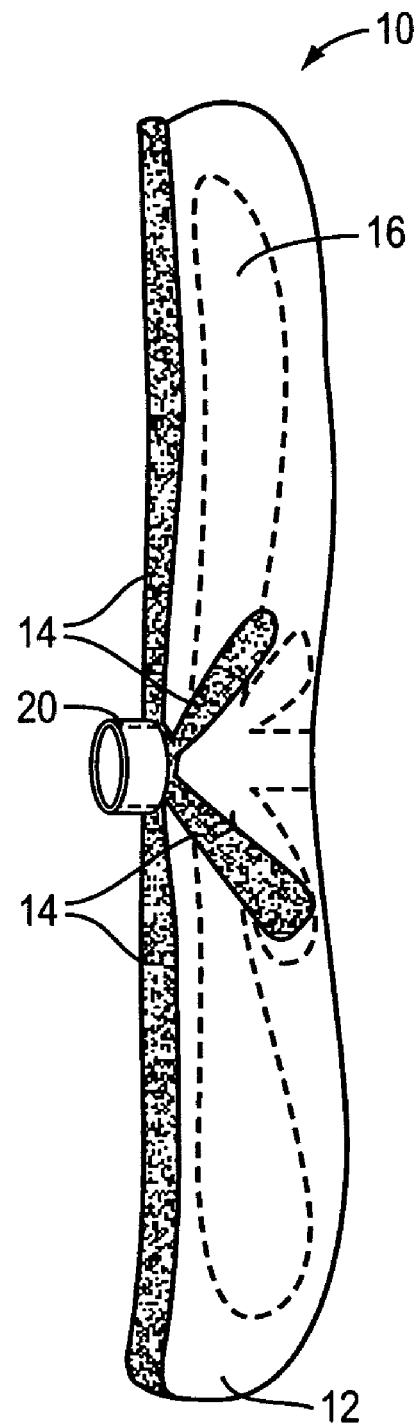
FIG. 2B is a side view of an illustrative embodiment of the inflatable occluder of the invention in FIG. 2A showing a single scaffold after it is inflated, at least one channel, four structural members, and an injection port.

FIG. 1A is a front view of an illustrative embodiment of an inflatable septal occluder 10 of the invention including one or more scaffolds 12, one or more channels 16, one or more structural members 14, and an injection port 20. As illustrated in FIGS. 2A-2B, in certain embodiments, for example, the occluder 10 includes only one scaffold 12.

Figure 1B:
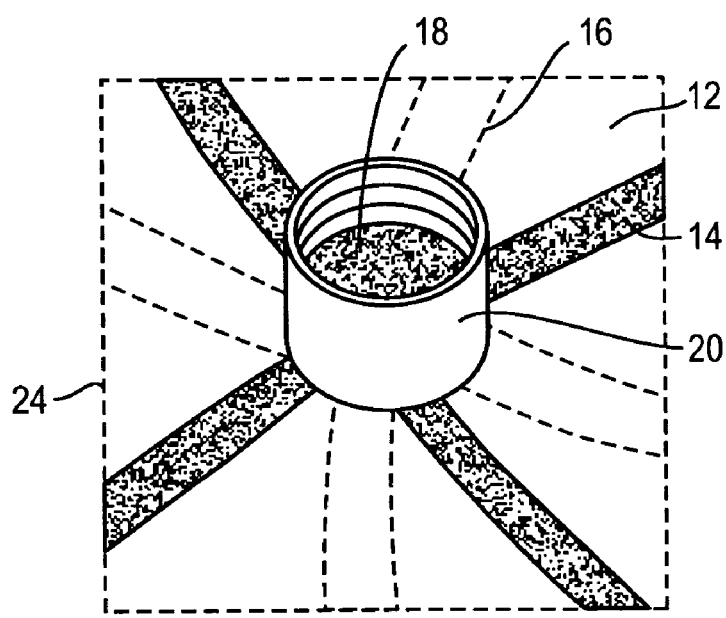
FIG. 1B is an exploded view of the center portion of FIG. 1A, illustrating an illustrative embodiment of the injection port of the invention including a threaded connection member.
Figure 3A:
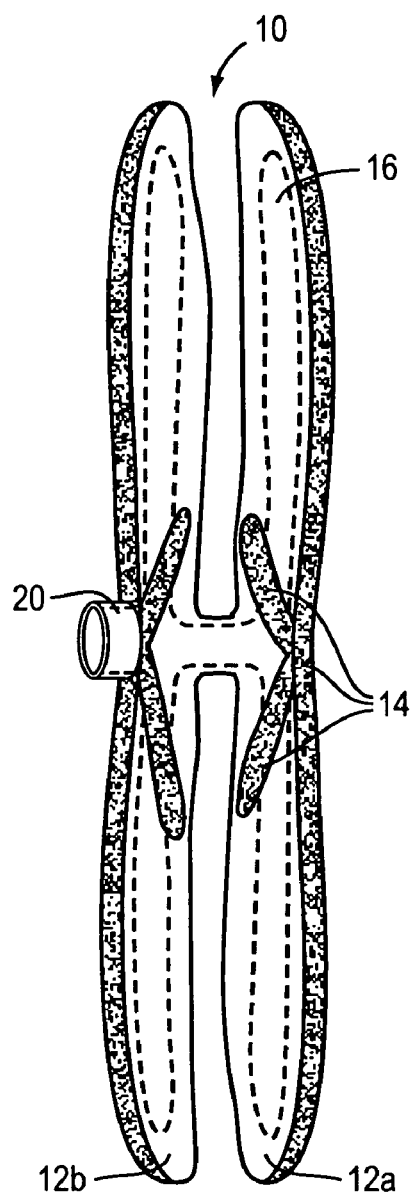
FIG. 3A is a side view of an illustrative embodiment of an inflatable occluder of the invention showing two scaffolds in fluid communication via a channel (not inflated), four channels, four structural members, and an injection port.

Alternatively, the occluder 10 may have two scaffolds 12A, 12B as shown in FIG. 3A. Referring to FIG. 1B, the injection port 20 is in fluid communication with one or more channels 16. As show in FIGS. 2A-2B, when a fluid is directed into the injection port 20, it flows into the channel 16, expands the channels 16 and thereby the scaffolds 12. The structural members 14 provide resistance to expansion of the scaffold(s) 12 such that, when the one or more channel 16 is inflated, the scaffold 12 adapts a shape suitable for occluding a septal defect. Other embodiments of the invention contemplate any number of channels 16 for inflating the tissue scaffold 12 and any number of structural members 14.

Referring again to FIG. 2A, illustrated is a side view of an exemplary embodiment of an inflatable occluder 10 of the invention including a scaffold 12 that is in a collapsed configuration. Upon injection of a fluid into the fluid inlet port 20 and through the one or more channels 16, the occluder 10 expands. As illustrated in FIG. 2B, according to an illustrative embodiment of the invention the structural member 14 provides resistance to expansion of the scaffold 12. As a consequence, in one embodiment, the structural member 14 becomes slightly bent near its free end upon expansion of the scaffold 12. The scaffold 12 adapts an enhanced shape capable of occluding a septal defect, such as a PFO.

Figure 3B:
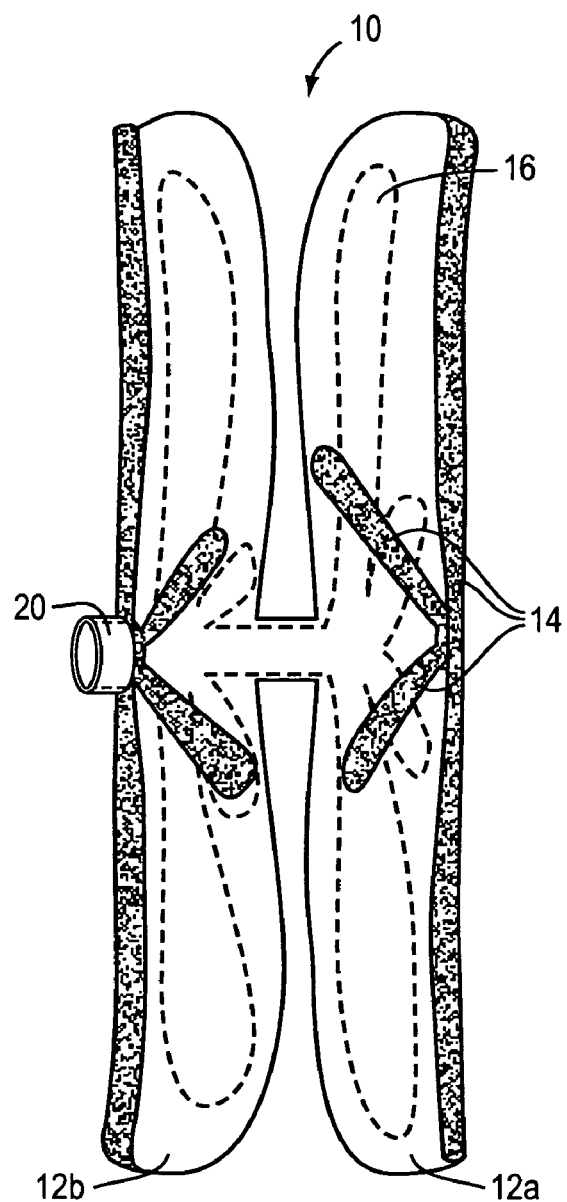
FIG. 3B is a side view of an illustrative embodiment of the inflatable occluder of the invention in FIG. 3A showing two inflated scaffolds in fluid communication via a channel, four channels, four structural members, and an injection port.

Referring again to FIG. 3A, a side view of an exemplary embodiment of an inflatable implant 10 of the invention including scaffolds 12A, 12B in a collapsed configuration is illustrated. The two scaffolds 12A, 12B are in fluid communication by means of channel 16. A fluid expands the occluder 10 when the fluid is injected into port 20 through the channel 16. FIG. 3B illustrates the occluder 10 in FIG. 3A in an inflated or expanded configuration. The structural members 14 provide resistance to distension of the scaffolds 12A, 12B, such that the structural members 14 become slightly bent near their free end upon expansion of the scaffold 12. The scaffolds 12A, 12B adapt a shape that is capable of occluding a septal defect, such as a PFO.

Referring again to FIG. 1A, the exemplary occluder 10 includes at least one structural member 14 that extends radially from the center of the scaffold 12 at the injection port 20 towards the periphery of the scaffold 12 where the structural member 14 terminates in a free end 15. The structural member 14 may be adhered, e.g., glued or stitched, to the scaffold 12 on the exterior or interior surface of one side of the scaffold 12. As used herein, exterior means away from the tissue surface and interior means on the side closest to the tissue surface.

In certain embodiments, the structural member 14 is a portion of the scaffold 12 that is thicker or that comprises a stiffer material that other portions of the scaffold 12. The structural member 14 may be made of, or coated with, for example, a metal or alloy, such as nitinol, stainless steel, or magnesium. In another embodiment, the structural member 14 may be made of, or coated with, for example, a polymer such as polyethylene, polyether-amide block copolymer (e.g., PEBAX®, Atofina Chemicals, Philadelphia, Pa.), polyurethane, and fluorinated ethylene propylene, for example. In certain embodiments, the structural member 14 is permanent when the occluder 10 is implanted, e.g., it is not bioresorbable. In another embodiment, the structural member 14 is temporary, i.e., the structural member 14 is bioresorbable and eventually resorbed by the patient's body.

Referring again to FIG. 1B, the injection port 20 provides a conduit for introducing a fluid into the one or more channels 16 of the scaffold 12. In a particular embodiment, the injection port 20 has a threaded member 18 by which the injection port 20 may be reversibly attached to an elongated member or catheter (not shown) for delivery of the occluder 10 into the heart. Alternatively, the injection port 20 connects to a catheter via a break away connection or a simple quick connection. In a particular embodiment, the injection port 20 may include a valve, e.g., a one-way valve to prevent back-flow of fluid out of the one or more channels 16. An exemplary one-way valve is a self-closing membrane similar to those found in needle injection ports of intravenous fluid bags.

Figure 4:
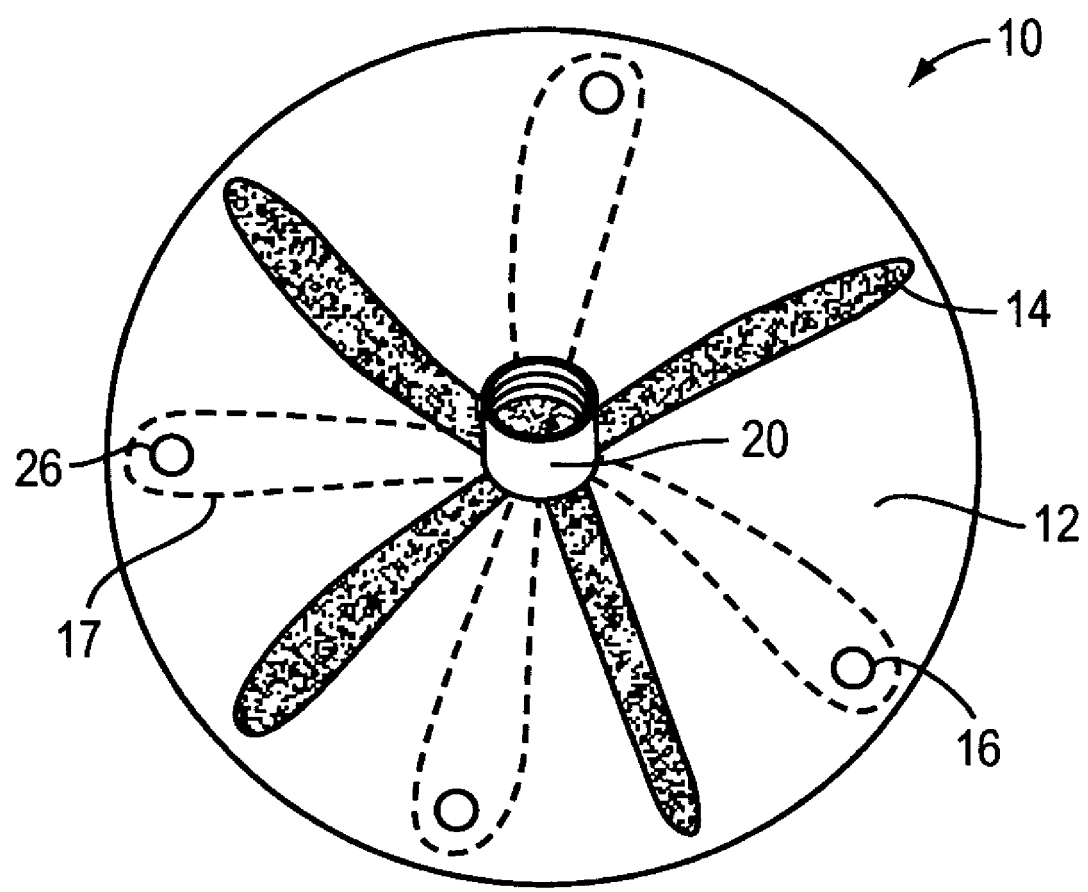
FIG. 4 is a front view of an illustrative embodiment of an inflatable occluder of the invention including a scaffold, four channels having a flush port at the distal end of each channel, four structural members, and an injection port.

FIG. 4 is a front view of an inflatable occluder including flush ports according to an illustrative embodiment of the invention. In the exemplary embodiment shown in FIG. 4, the tissue scaffold 12 includes at least one flush port 26 at the distal end 17 of at least one channel 16. The flush port 26 is in fluid communication with the channel lumen and the exterior of the occluder. The flush port 26 is useful for removing fluid from the scaffold 12, either before, during, or after inflation or deflation of the scaffold 12, if desired. In an embodiment, the flush port includes a valve, e.g., a one-way valve.

Referring again to FIGS. 1A-1B, in the exemplary embodiment, the scaffold 12 is disc-shaped. Alternatively, the scaffold 12 is cup-shaped or may be clover-shaped with, for example, three or more petals (not shown). The scaffold 12 is made from, for example, a non-bioresorbable polymer such as polyethylene, polyether-amide block copolymer (e.g., PEBAX®, Atofina Chemicals, Philadelphia, Pa.), polyurethane, fluorinated ethylene propylene, expanded polytetrafluoroethylene (EPTFE), polyester fabric, polyvinyl alcohol or a bioresorbable material such as polylactic acid, polyethyleneglycol, polyglycolicacid, polycaprolactone, or polydioxanone, collagen, gelatin, albumin, carbohydrates, polyphosphazene, low molecular weight aliphatic polyesters, or any bioresorbable adhesive, or any combination of the above materials.

In one embodiment, a polymer, for example nylon, with the ability to stretch with a lower modulus, imparts to the occluder an ability to stretch to fill the anatomical defect, e.g., a PFO. Alternatively, the material used to make the occluder 10 may be noncompliant such as, for example, polyethylene terathalate and may be comprised of thin polymer fibers woven into an impermeable or semipermeable mesh. Fibers that are applicable for this purpose are, for example, collagen, lactides, glycolides, or coweaves of such materials.

In an exemplary embodiment, the scaffold 12 is a solid material which is bored through by drilling, or molded to form the channels 16. In certain embodiments, the occluder 10 includes a single scaffold 12 or, alternatively, includes two tissue scaffolds 12A, 12B that are substantially disc-shape. The scaffolds 12A, 12B are sized and shaped when inflated to occlude a septal defect, such as a patent foramen ovale (PFO), atrial septal defect (ASD), ventricular septal defect (VSD), left atrial appendage (LAA), or patent ductus arteriosus (PDA).

In one embodiment according to the invention, the scaffold 12 of the occluder 10 includes a meshwork. Accordingly, the meshwork may include polyethylene terathalate (PET), or polytetrafluoroethylene (PTFE), or a bioresorbable material, for example, caprolactone or polylactic acid or a combination of the above materials. In a particular embodiment the bioresorbable material may include fibers of, for example, polylactic acid, polyglycolic acid, collagen, chondroitin sulfate, or coweaving of any of these materials. The meshwork features, for example, several layers of a knit or weave. These materials induce the patient's own tissues to generate cellular and fibrillar overgrowth forming a wall of cellular and/or fibrillar tissue that is capable of resisting the pressure difference between the right and left chambers of the heart in a patient with a PFO.

In a particular embodiment, the occluder 10 is, for example, a single scaffold 12 made by joining a first layer of material and a second layer of material. The layers of material may be made from the same or different materials. For example, in one embodiment the materials differ in one or more mechanical properties such as tensile strength, flex modulus, extension to break, thickness, and durometer, or differ in surface geometry and cross section. In an exemplary embodiment, the first layer of the scaffold on the outer surface is coated or applied with an adhesive, for example, any of the adhesives in Table I such as cyanoacrylate, fibrin based adhesive, light activated adhesive, albumin and gluteraldehyde based adhesive, fibrin, collagen or thrombin-based adhesives, polyethylene glycol (PEG) polymer based adhesive, or marine derived adhesives for adhering to the septal defect. For example, marine-derived proteins, are proteins secreted by marine mussels, barnacles, and coral reef building worms including protein precursors that are cross-linked ("cured") into a hardened matrix that include high levels of 3,4-dihydroxyphenylalanine (DOPA, a known metal chelator).

TABLE I

TISSUE ADHESIVES

| Manufacturer | Name of Product | Type |
| --- | --- | --- |
| Angiotech (Vancouver, B.C.) | CoStasis ® | collagen/thrombin |
| Closure Medical (Raleigh, N.C.) | N/A | cyanoacrylate |
| Cordis (Miami Lakes, FL) | Trufil ® | cyanoacrylate |
| US Surgical (Norwalk, CT | Indermil ® | cyanoacrylate |
| Baxter (Deerfield, IL) | Tisseel ® | fibrin based |
| Baxter (Deerfield, IL) | FloSeal ® | fibrin based |
| Vivolution (Birkeroed, Denmark) | Vivostat ® | fibrin based |
| Genzyme (Cambridge, MA) | FocalSeal ® | PEG polymer |
| Berlin Heart (Berlin, Germany) | Glue Tiss ® | resorcinol based |
| Biota, Ltd. (Melborne, Australia) | Mussel glue | marine based |

In a particular embodiment, one or more channels 16 are positioned between the inner and outer layers of the scaffold. Alternatively, the channels 16 are positioned on the outside layers. In certain embodiments, the channels 16 have a cross-sectional shape selected from the group consisting of linear, circular, cross-shaped, spiral-shaped, and star-shaped, but may have any suitable shape such that the occluder 10 occludes a septal defect when the occluder is positioned in the septal defect and the one or more channels 16 are inflated.

In certain embodiments, a fluid is introduced into a channel of an occluder. The fluid may be a liquid, a gas, or combinations thereof. The fluid can be a gas such as an inert gas that is directly introduced into the channel or the fluid can be a gas that is formed in situ to facilitate the inflation of the scaffold. An example of the latter is the production of carbon dioxide in the making of polyurethane foam. In such an embodiment, the port of the channel may be sealed prior to generation of the gas or the port may remain open at least partially to regulate the inflation of the occluder by permitting excess gas to be controllably bled from the channel.

In other embodiments, the fluid can be a liquid. The fluids can contain buffers, antimicrobial agents, chelators, growth factors, and the like depending on the particular application. For example, the fluid can be a saline solution, which may be at a particular pH and/or contain antimicrobial agents. As appreciated by a skilled artisan, any biocompatible fluids can be used and in particular, those fluids commonly used in the field of cosmetic surgery, e.g., silicone.

The liquid can be a flowable or molten material and/or may include solid particulates and other materials which may be substrates for chemical reactions after their introduction in the channel. The solid particulates also can be present as a filler. For example, microbeads made of a cross-linked water swelling material, e.g., polyvinylpyrrolidone, may be used. Cross-linked microbeads, e.g., FloSeal® (Baxter, Deerfield, Ill.), swell many times their original size when mixed with water. These materials may be injected into a channel along with the fluid.

In some embodiments, a fluid is or contains a polymerization system, i.e., the fluid is a polymer itself, or includes a polymer, monomer, cross-linkers, and/or initiators. The polymerization system can be converted to a semi-solid, e.g., a hydrogel, or to a solid after its introduction into the channel.

In a multi-part polymerization system, certain of the reaction components can be present within the channel prior to introduction of the occluder into the patient. Subsequent to the occluder being properly positioned, the other component(s) of the polymerization system are introduced into the channel, which may spontaneously initiate the polymerization reaction. In other similar embodiments, the polymerization reaction requires an additional initiator, e.g., a catalyst that creates free radicals; light such as ultraviolet light or laser light, which could be introduced into a channel through an optical fiber; or heat, which could be introduced into a channel via a heat probe.

Examples of polymers and polymerization systems useful in the practice of the invention include, but are not limited to, polyphosphazenes, polyethylene glycols, polybutadienes, polyacrylates, polydiacrylates, polyurethanes, polyacrylamides, polyvinylpyrrolidone, collagen, carbohydrates such as chitosan, polylysines, polylactic acids, and combinations thereof.

It should be understood that the particular application and/or materials of construction of the system will influence the choice of a fluid to inflate the occluder as well as whether the fluid is modified or altered to produce a different material having the desired properties for practicing the invention. That is, the end properties of the occluder often will dictate the fluid to be used to inflate the occluder. For example, for a rigid occluder, a combination of solid particulates, liquid and gas generated in situ may be employed as the occluder will take on the shape of its surrounding environment during formation of the gas. A rigid occluder also can be formed using flowable liquid monomers and/or polymers, which can be further polymerized and/or cross-linked to produce a stiff polymeric material. To this end, the amount and concentration of the polymerization components, e.g., monomer(s), polymer(s), cross-linker(s) and polymerization initiator(s), can be controlled to produce an end product that has the desired properties. However, in certain embodiments, the fluid itself possesses the characteristics that are desired for the final product, e.g., viscosity, density, compressibility, and biocompatibility.

In another embodiments according to the invention, the third, e.g., a polymeric material, introduced into the one or more channels of the occluder is an adhesive, such as cyanocrylate; a fibrin-based adhesive; a light-activated adhesive; albumin; a gluteraldehyde-based adhesive; a polyethylene glycol (PEG) polymer-based adhesive; and a marine-derived adhesive. In other embodiments, the polymeric material introduced into one or more channels of the occluder is a bioresorbable material such as collagen, gelatin, albumin, carbohydrates, polyphosphazene, low molecular weight aliphatic polyesters, and a bioresorbable adhesive, or combinations of the above. In another embodiment, bioresorbable materials introduced into one or more channels of the occluder include polycaprolactone, and polyvalerolactone with copolymers of lactides.

In certain embodiments according to the invention, bioreactive materials are introduced into the one or more channels of the occluder. Bioreactive materials include, but are not limited to, growth factors, angiogenic factors, stem cells, nucleic acids, cellular adhesive molecules, fibronectin, vitronectin, collagen, fibrin, and any combination of the above.

Biological materials in fibrous form, for example CoStasis® (Angiotech, Vancouver, B.C.), may be woven into the meshwork of the scaffold of the occluder or deposited onto the surface of the meshwork. Chemical bonds may form between blood plasma, activated PET, or PTFE to stimulate ingrowth of the patient's tissue.

In yet another embodiment, non-gas forming materials may be used for introduction into one or more channels of the occluder. For example, microbeads made of a cross-linked water swelling material, for example, polyvinylpyrrolidone (PVP) may be used. Cross-linked microbeads, for example, FloSeal® (Baxter, Deerfield, Ill.), swell many times their original size when mixed with water. These materials may be injected into the occluder carried with a stabilizing material. Alternatively, collagen or combinations of collagens, carbohydrates and PVP may be used as a non-gas forming material.

In one embodiment, according to the invention, the carrier or stabilizer material used with the material introduced into the one or more channels of the occluder includes the isocyanates mentioned above, or materials that form chemical bonds by free radical addition. For example, acrylates and acrylamides are introduced into the one or more channels of the occluder in solution and are subsequently activated with heat or light in the presence of an initiator. The heat or light energy is supplied by an optic fiber or heated probe positioned in the injection lumen at the port of the occluder. Combinations of swelling material, for example, collagen or PVP microbeads, and acrylates or diacrylates, for example, neopentyldiacrylates may be used in the injectable materials.

FIGS. 5A-5E depict a plan view of an implant delivery system 30 according to an illustrative embodiment of the invention in combination. The illustrative implant delivery system 30 includes a catheter 36 that is axially slideable in the lumen 40 of a sheath 34. A coupling mechanism 38 at the distal end 33 of the catheter 36 couples the catheter 36 to the occluder 10 at or near the injection port 20 on the occluder 10. The illustrative coupling mechanism 38 includes, for example, a threaded device. Alternatively, other coupling mechanisms, for example, ball-to-ball or grasper members, or a magnetic mechanism, may be used. The catheter 36 includes a proximal end 39 operatively connected to an actuator 41 on a handle 37, and a distal end 33 joined to the coupling mechanism 38.

With continued reference to FIGS. 5A through 5E, in another embodiment according to the invention, the catheter 36 is slideably movable in the lumen 40 of the sheath 34. For example, the sliding of the catheter 36 in a fixed sheath 34, or alternatively, the sliding of the sheath 34 while the catheter 36 is stationary, is controlled by the actuator button 41 on the handle 37. Accordingly, the proximal end 39 of the catheter 36, for example, is operatively joined to the actuator button 41 in the handle 37. Alternatively, the catheter 36 is fixed in position and the sheath 34 is operatively joined to the actuator button 41 in the handle 37 for slideable movement over the stationary catheter 36.

In another aspect, the present invention includes methods for delivering and withdrawing an occluder from a patient. FIGS. 5A-5E depict the steps in delivering a single scaffold 12 occluder 10 by the delivery device 30.

Figure 5A:
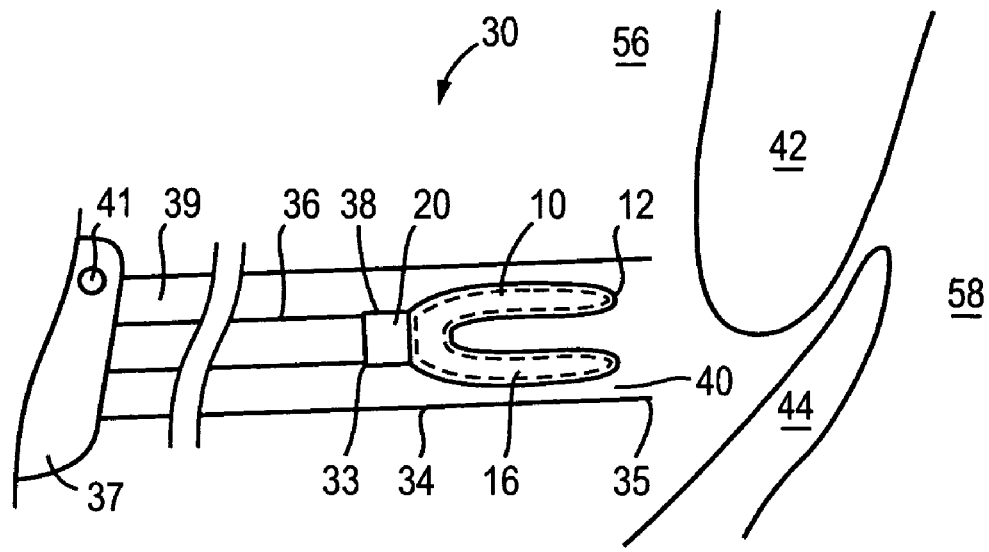
FIGS. 5A-5E depict a method for delivery of an inflatable occluder having a single scaffold, to occlude a patent foramen ovale, according to an illustrative embodiment of the invention.

Referring to FIG. 5A, according to the invention, to deliver the occluder to an anatomical site, for example, a PFO, the operator introduces the delivery system 30 via a transluminal percutaneous route, for example via the femoral vein, into the patient and extends the implant delivery system 30 including sheath 34, the catheter 36 having a distal end 33 coupled to the occluder 10, as described above, into the right atrium. In the illustrative embodiment, the occluder 10 is collapsed in the sheath 34 with the center 100 of the occluder 10 more proximal relative to the operator than the margins of the occluder 10.

Figure 5B:
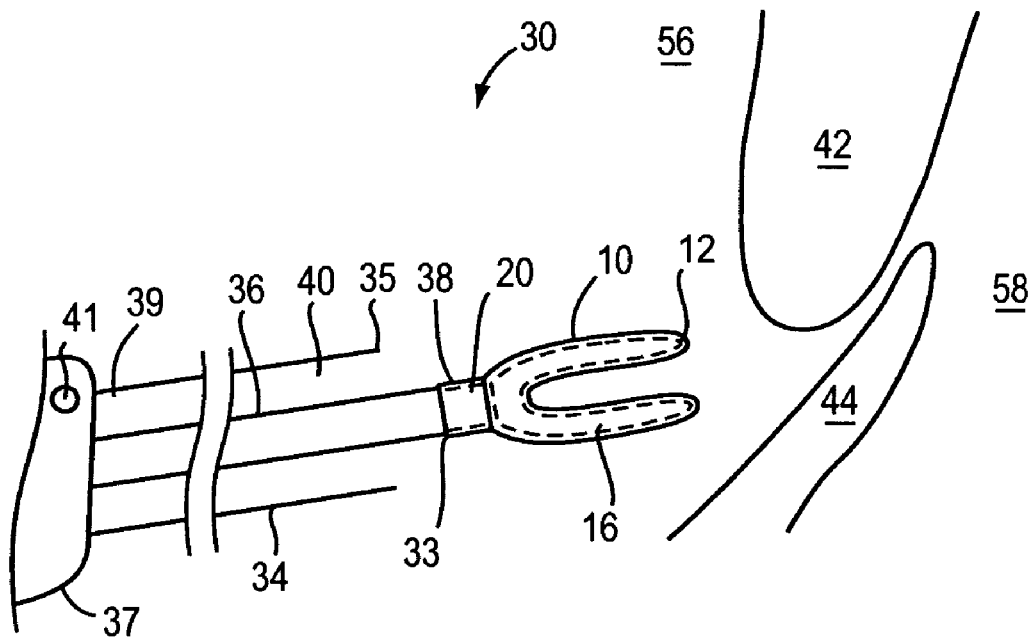
Figure 5C:
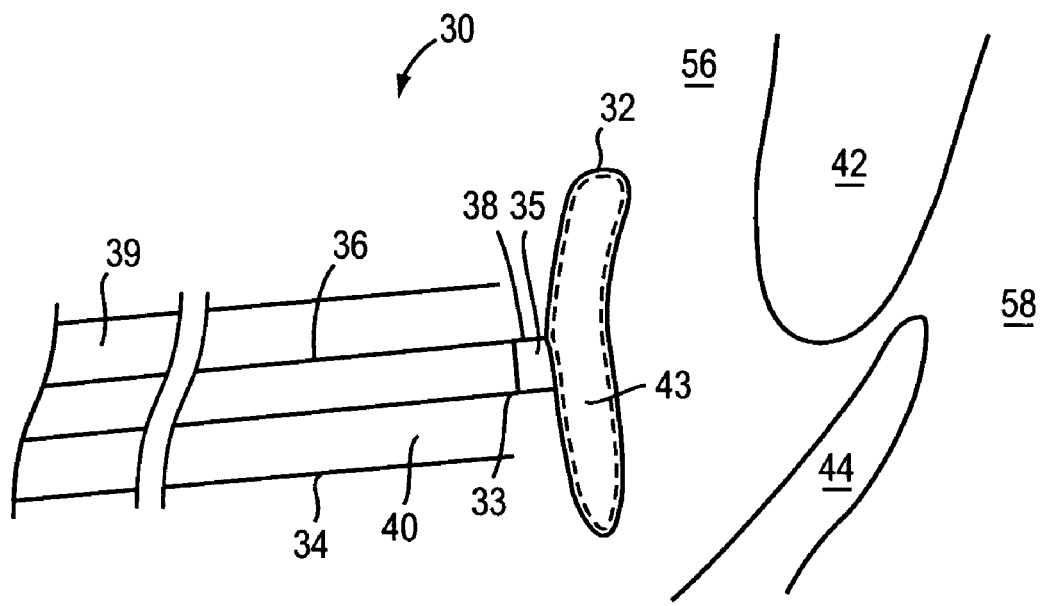
Figure 5D:
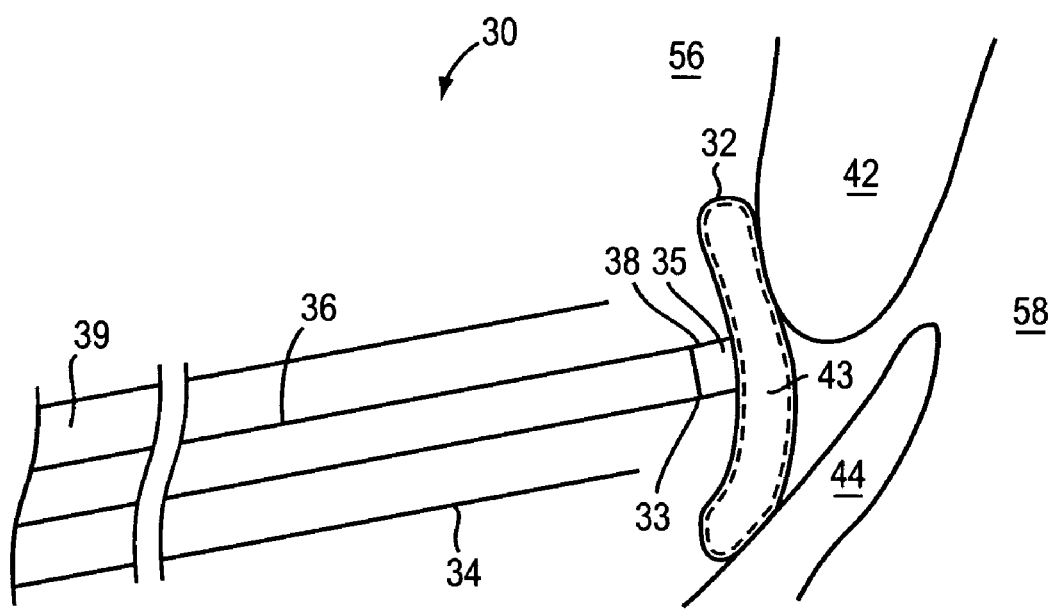

Referring now to FIG. 5B, the occluder 10 is positioned beyond the distal end 35 of the sheath 34 by transitioning the occluder 10 from the lumen 40 of the sheath 34 to beyond the distal end of the sheath 34 whereby the scaffold 12 is deployed. Once the scaffold 12 of the occluder 10 is satisfactorily positioned within the right atrium adjacent the PFO, for example, the operator expands the one or more channels 16, as illustrated in FIG. 5C, by introducing a fluid, e.g., the materials described above, through the catheter 36, the injection port 35, and into the channels 16. Referring to FIG. 5D, the expanded scaffold 12 engages the two over-lapping layers of tissue forming the PFO, i.e., the septum primum 44 and septum secundum 42, when the operator manipulates the occluder 10 with the catheter.

Figure 5E:
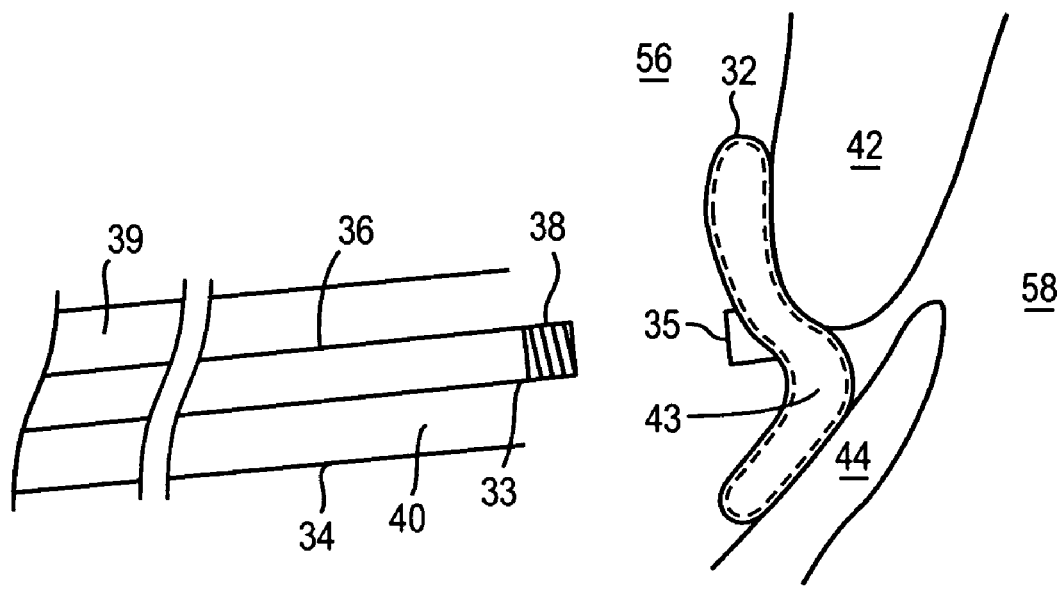

Referring now to FIG. 5E, the operator releases the occluder from the catheter 36, e.g., by actuating the button 41 on the handle 37 to transition the coupling mechanism 38 into an open or disengaged position to disconnect the coupling mechanism 38 from the occluder 10. If the operator is dissatisfied with the positioning of the scaffold 12, the scaffold 12 may be recaptured and withdrawn into the lumen 40 of the sheath 34 by engaging the coupling mechanism 38 with the occluder 10.

In a particular embodiment, the scaffold 12 and/or the channels 16 include one or more pores (not shown) that extend from the lumen of the channel 16 to the exterior surface of the scaffold 12. Fluids that are injected into the channel, for example, an adhesive, leaks, weeps, or leaches out of the channel 16 via the pores to the exterior surface of the tissue 12. The tissue 12 adheres to the scaffold 12 in the presence of the adhesive on the scaffold surface.

Figure 5F:
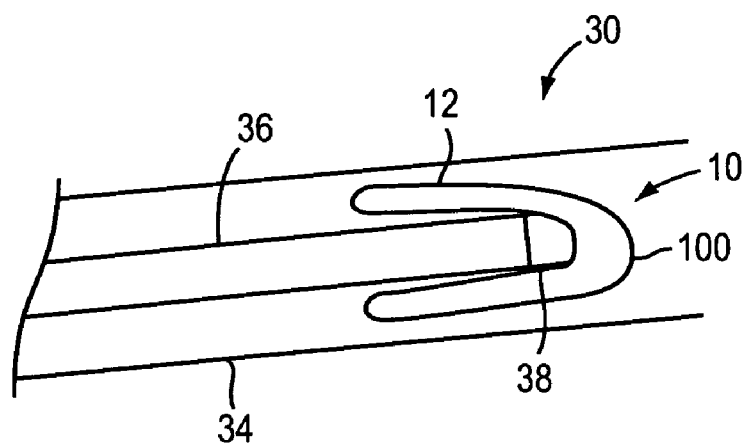
FIG. 5F is a side view of an inflatable occluder including a single scaffold in an arrowhead orientation within the delivery sheath according to an illustrative embodiment of the invention

Referring to FIG. 5F, according to another embodiment of the invention, during delivery the occluder 10 is collapsed in the sheath 34 with the center 100 of the occluder 10 more distal relative to the operator than the margins of the occluder 10.

Figure 6A:
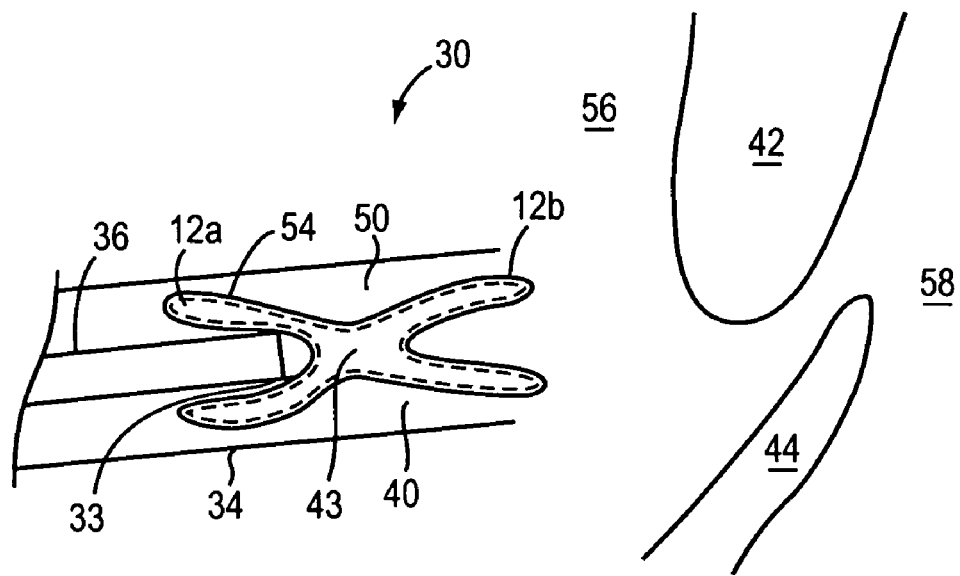
FIGS. 6A-6G depict a method for delivery of an inflatable occluder having two scaffolds, to occlude a patent foramen ovale, according to an illustrative embodiment of the invention.
Figure 6B:
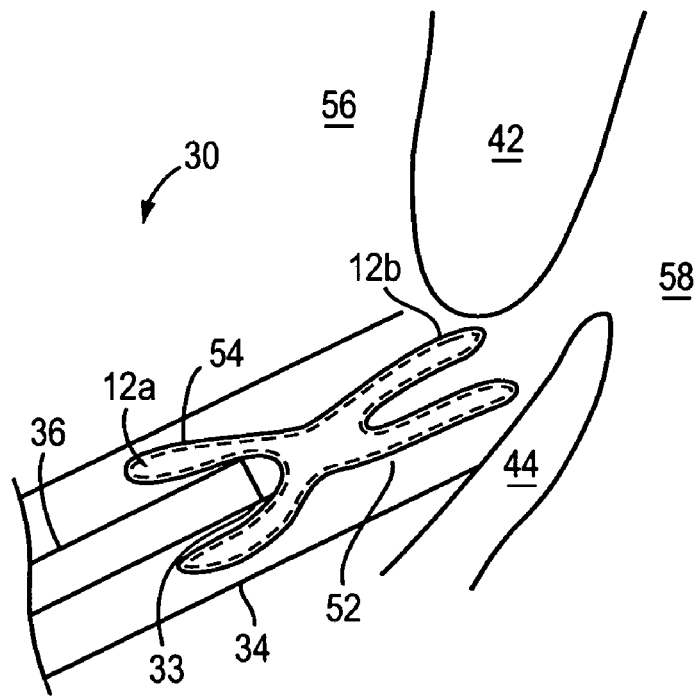
Figure 6C:
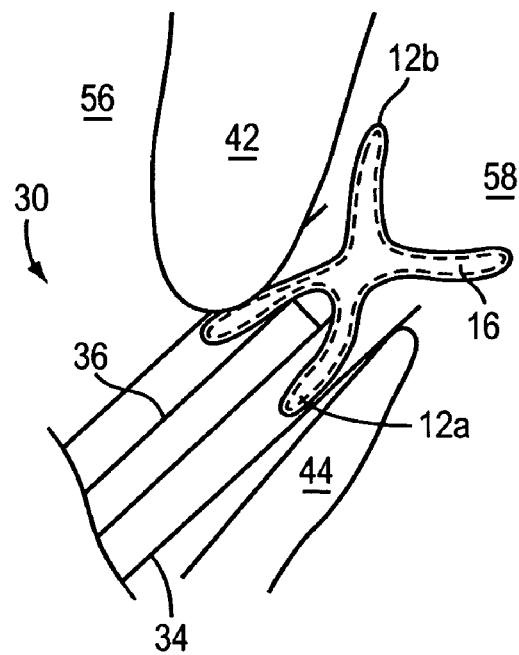
Figure 6D:
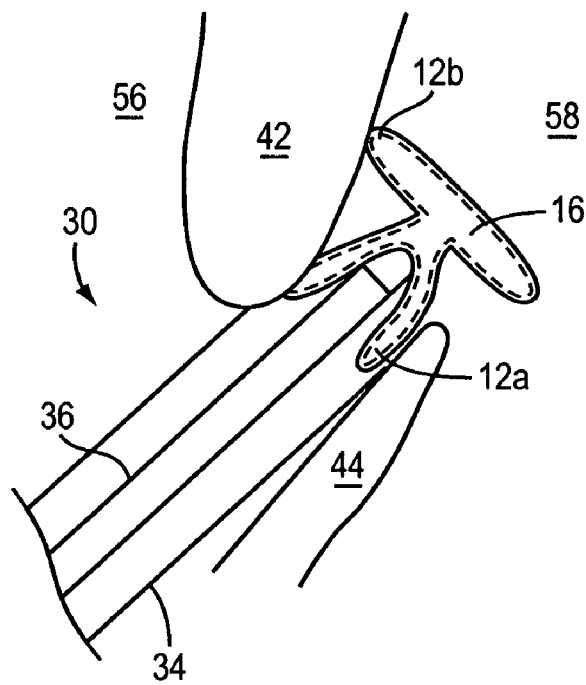
Figure 6E:
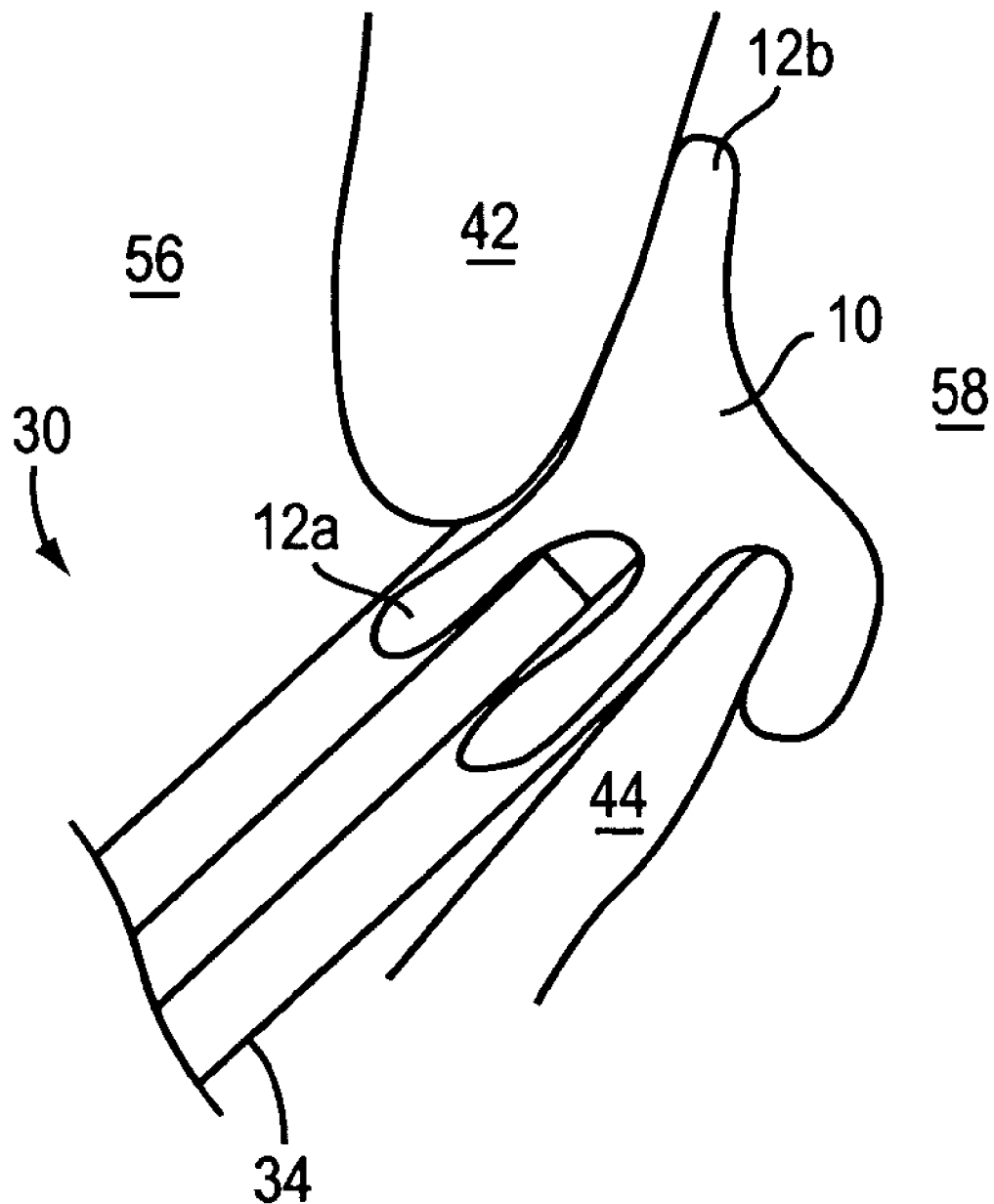
Figure 6F:
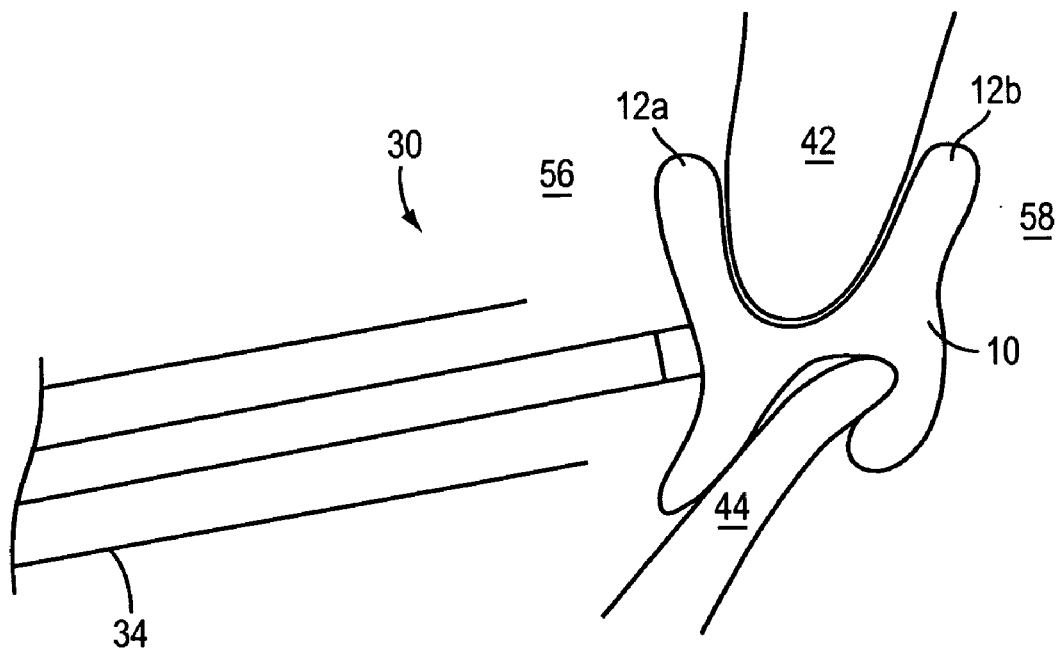
Figure 6G:
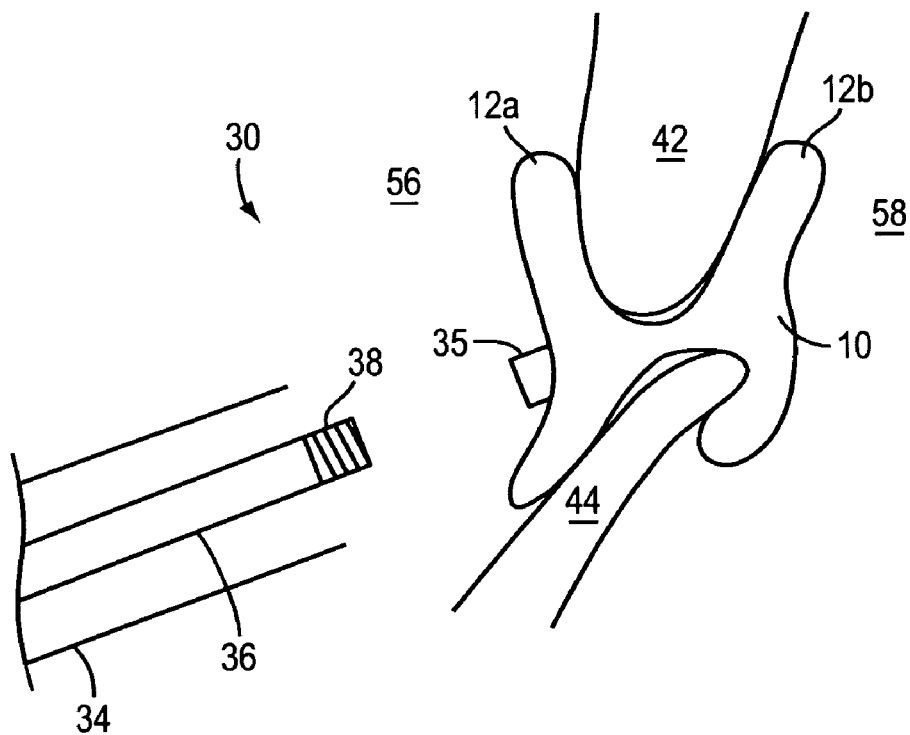

FIGS. 6A-6E depict the steps in delivering an occluder 12 including opposing distal tissue scaffold 12b and proximal tissue scaffold 12a, by an implant delivery device 30, according to an illustrative embodiment of the invention. Referring to FIG. 6A, the implant delivery system 30 includes a catheter 36 slideably moveable within a lumen 40 of a sheath 34, and a catheter distal end 33 coupled to the occluder 12. In the illustrative embodiment, the occluder 10 is collapsed in the sheath 34 with the center 100 of the occluder 10 more proximal relative to the operator than the margins of the occluder 10. The operator introduces the sheath 34 into the patient via a percutaneous transluminal route, for example, the femoral vein, and extends the occluder 10 into the right atrium 56 through the PFO into the left atrium as illustrated in FIGS. 6B-6C. The sheath 34 is transitioned whereby the distal scaffold 12b is deployed beyond the distal end of the sheath 34 in the left atrium 58. Following satisfactory positioning of distal scaffold 12b within the left atrium 58, the operator expands the distal scaffold 12b as illustrated in FIG. 6D by introducing a fluid, for example, fluid's such as those described above, into the catheter 36 via the injection port 35 and into the channels 16. The distal scaffold 12b is applied to the left atrium side of the two over-lapping layers of tissue of the PFO, i.e., the septum primum 42 and septum secundum 44 in the left atrium 58. Referring to FIG. 6E, the distal end of the sheath 34 is withdrawn from the left atrium 58 into the right atrium 56 and transitioned to deploy the proximal scaffold 12a beyond the distal end of the sheath 34. Referring to FIG. 6F, the proximal tissue scaffold 12a expands by further introduction of the fluid through the injection port 35 and into the channels 16 of the proximal scaffold 12a. The occluder 10 is released from the catheter 36 as shown in FIG. 6G, e.g., by actuating button a 41 on the handle 37 to transition the coupling mechanism 38 into an open or disengaged position to disconnect the coupling mechanism 38 from the occluder 10.

Figure 6H:
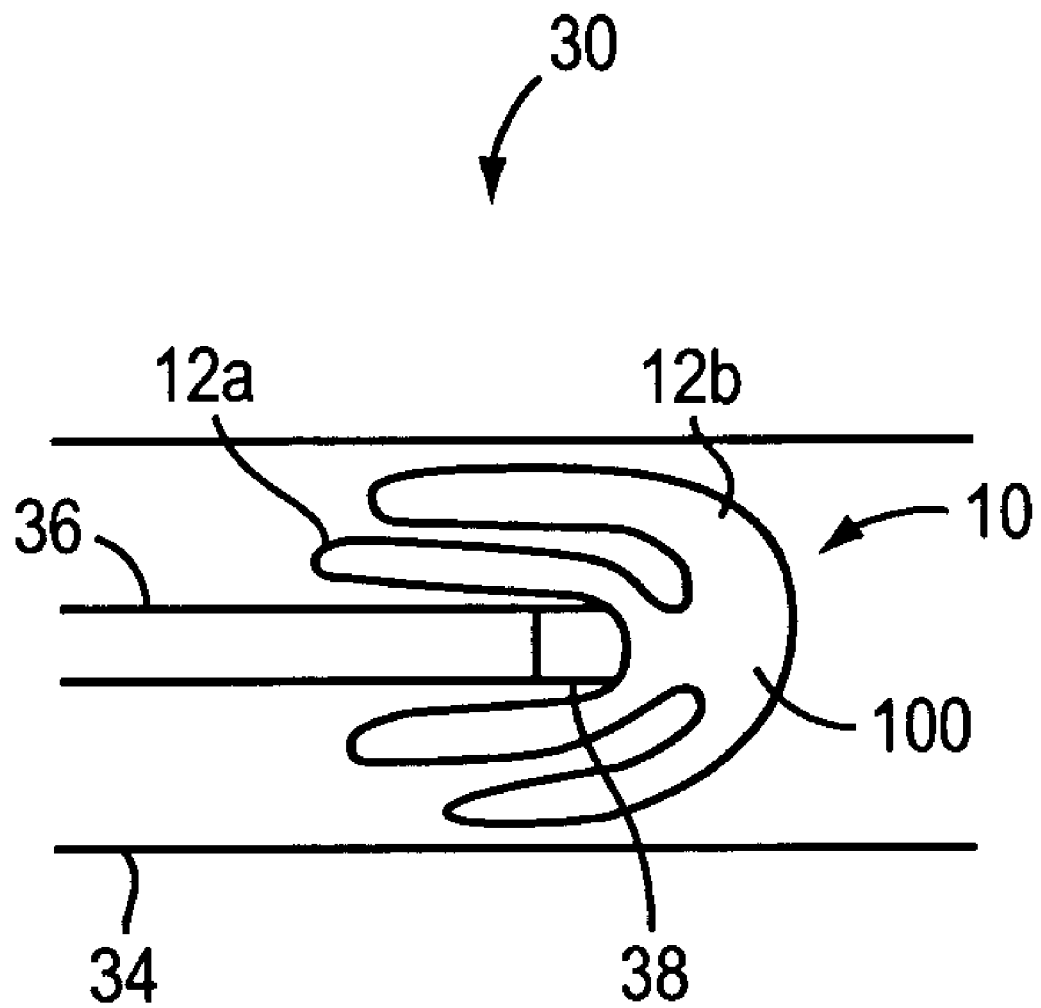
FIG. 6H is a side view of an inflatable implant including two scaffolds in a double arrowhead orientation within the delivery sheath according to an illustrative embodiment of the invention.

Referring to FIG. 6H, according to another embodiment of the invention, during delivery, the occluder 10 is collapsed in the sheath 34 with the center 100 of the occluder 10 more distal relative to the operator than the margins of the occluder.

In a particular embodiment according to the invention, after the occluder is positioned at the anatomical site, e.g., a PFO, being treated, the occluder 10 is transitioned in situ from a substantially compliant occluder to a substantially rigid occluder. For example, an injectable third material, such as the materials described above, is introduced into the one or more channels 16 of the occluder 10. The injectable third material, e.g., injectable polymeric material, may be hardened, for example, by alterations in pH effected by infusion of solution through the catheter 36 having a pH that differs from the pH of the original solution. Alternatively, the injectable third material may be hardened by the addition of heat, light, ions, and/or an organic solvent.

Alternatively, according to yet another embodiment of the invention, the occluder 10 transitions to a substantially rigid state through the cooperative effects of coagulation, precipitation, or ionization of the patient's blood in proximity of the occluder 10. For example, the portion of the occluder 10 contacting the atrial septal wall may comprise fibrinogen, which crosslinks once it comes into contact with thrombin in the patient's blood. Alternatively, a solution including thrombin may be pumped from the catheter 36 into the one or more channels of the occluder 10.

In a particular embodiment according to the invention, the cross-linking material introduced into the one or more channels 16 of the occluder 10 may be permeated with biological components such as chemotactic or growth factors for example, angiogenic factors, stem cells, nucleic acids, cellular adhesive molecules, fibronectin, vitronectin, collagen, and fibrin, or any combination of the above that alter the reaction of the surrounding tissue. For example, the chemotactic or growth factors may induce the patient's tissue to grow into the occluder.

According to an embodiment of the invention, the injectable materials including crosslinkable moieties that are introduced into the chamber 16 of the scaffold 12 of the occluder 10 may be hardened or stiffened by heat or light. Thus, collagen, carbohydrates, polylactic or polyglycolic acid or combinations of these may be copolymerized with acrylic acid, butadiene or other agents containing reactive double bonds. These homopolymers or copolymers may also contain more mobile low molecular weight polymers that react with the side chains of the main polymer. After transition of the occluder into the appropriate shape, energy is applied to the infected material to crosslink and thereby harden or stiffen the material.

The route by which the cardiac defects are accessed via catheter are well known in the art. For example, for treatment of a PFO, the catheter may be introduced via the femoral vein by standard art known methods and guided into the right atrium. A sizing balloon is optionally used to determine the size of the defect prior to insertion of an implant, according to art known methods. The surgical procedure used to access the right atrium is standard to any cardiac catheterization laboratory. Other routes of entry will depend upon the location of the defect.

The invention may be embodied in other specific forms without departing from the spirit or essential characteristics thereof. The foregoing embodiments are therefore to be considered in all respects illustrative rather than limiting on the invention described herein.

All publications and patent documents cited in this application are incorporated by reference in their entirety for all purposes to the same extent as if the contents of each individual publication or patent document was incorporated herein.

What is claimed is:

1. A system for closing of an intracardiac defect, comprising:
    a first scaffold enclosing at least one first channel, said first channel comprising a lumen;
    a second scaffold enclosing at least one second channel, said second channel comprising a lumen;
    an injection port connectable to a catheter and in fluid communication with the lumen of the first channel and the lumen of the second channel and the catheter, wherein the lumen of the first channel and the lumen of the second channel are in fluid communication; and
    a structural member associated with the first scaffold extending radially from a center of the first scaffold toward a margin of the first scaffold and configured to provide resistance to expansion of the scaffold such that the structural members become slightly bent near their free end upon expansion of the scaffold, wherein the structural member comprise a portion of the scaffold that is thicker than another portion of the scaffold which provide resistance to expansion of the scaffold, wherein a fluid introduced into the injection port flows into the channels thereby expanding the scaffolds.

2. The system of claim 1 wherein the second scaffold further comprises a structural member extending radially from a center of the second scaffold toward a margin of the second scaffold.

3. The system of claim 1 further comprising a plurality of first channels.

4. The system of claim 1 further comprising an injectable fluid, wherein the injectable fluid becomes a solid after introduction into the channels of the scaffolds.

5. The system of claim 4 wherein the injectable fluid comprises a bioresorbable material.

6. The system of claim 1 wherein the scaffolds comprise a bioresorbable material.

7. The system of claim 1 wherein the scaffolds comprise a first layer and a second layer.

8. The system of claim 7 wherein the channels are positioned between the first layer and the second layer.

9. The system of claim 1 wherein the injection port further comprises a connection member.

10. The system of claim 1 wherein the structural members comprise a curve.

11. The system of claim 1 wherein the structural members comprise a polymer.

12. The system of claim 1 wherein at least one channel further comprises at least one pore.

13. The system of claim 12 further comprising an adhesive wherein the adhesive flows from the at least one pore onto the outer surface of the scaffolds.

14. The system of claim 1 wherein at least one channel further comprises a flush port positioned at the distal end of the channel.

15. The system of claim 14 wherein the flush port further comprises a valve.

16. The system of claim 7 wherein the first layer of the scaffold comprises a first material and the second layer of the scaffold comprises another material.

17. A method for closing an intracardiac defect, comprising:
    positioning a compliant occluder adjacent the intracardiac defect in need of repair, the occluder comprising a first scaffold, a second scaffold, an injection port, and a structural member extending radially from a center of the first scaffolds toward a margin of the first scaffold and is configured to provide resistance to expansion of the scaffold such that the structural member become slightly bent near their free end upon expansion of the scaffold, wherein the structural member comprise a portion of the scaffold that is thicker than another portion of the scaffold which provide resistance to expansion of the scaffold, the scaffolds each comprising at least one channel, wherein the at least two channels are in fluid communication;
    expanding the channels of the scaffolds with an injectable fluid; and;
    solidifying the injectable fluid in the channels of the scaffolds whereby the occluder transitions from the compliant occluder to a rigid occluder to repair the intracardiac defect.

18. The system of claim 3 further comprising a plurality of second channels.

19. The system of claim 1 wherein the channels comprise a cross-sectional shape selected from the group consisting of: linear, circular, cross-shaped, spiral-shaped, and star-shaped.

* * * * *